US012625135B2

(12) United States Patent
Mower

(10) Patent No.: US 12,625,135 B2
(45) Date of Patent: May 12, 2026

(54) SYSTEM, APPARATUS, AND METHOD FOR VIRAL MONITORING IN EFFLUENT

(71) Applicant: Morton M. Mower, Denver, CO (US)

(72) Inventor: Morton M. Mower, Denver, CO (US)

( * ) Notice: Subject to any disclaimer, the term of this patent is extended or adjusted under 35 U.S.C. 154(b) by 0 days.

(21) Appl. No.: 17/539,763

(22) Filed: Dec. 1, 2021

(65) Prior Publication Data

US 2022/0113306 A1 Apr. 14, 2022

Related U.S. Application Data

(63) Continuation of application No. 17/070,308, filed on Oct. 14, 2020, now abandoned.

(51) Int. Cl.

| | |
|---|---|
| *G01N 27/414* | (2006.01) |
| *B82Y 15/00* | (2011.01) |
| *G01N 27/49* | (2006.01) |
| *G01N 33/543* | (2006.01) |

(52) U.S. Cl.
CPC ... *G01N 33/54373* (2013.01); *G01N 27/4145* (2013.01); *G01N 27/4146* (2013.01); *B82Y 15/00* (2013.01)

(58) Field of Classification Search
None
See application file for complete search history.

(56) References Cited

U.S. PATENT DOCUMENTS 3,832,574 A * 8/1974 Leehan ................ H03K 19/017
326/119

6,511,854 B1 * 1/2003 Asanov ............ G01N 33/54393
436/805

9,676,621 B2 6/2017 Chen et al.
(Continued)

FOREIGN PATENT DOCUMENTS

| | | |
|---|---|---|
| CN | 103649739 A | 3/2014 |
| JP | 2004-129548 A | 4/2004 |

(Continued)

OTHER PUBLICATIONS

Sinclair et al. (Pathogen Surveillance Through Monitoring of Sewer Systems, Advances in Applied Microbology, vol. 65, pp. 249-266, 2008) (Year: 2008).*

(Continued)

*Primary Examiner* — Neil N Turk
(74) *Attorney, Agent, or Firm* — Oblon, McClelland, Maier & Neustadt, L.L.P.

(57) ABSTRACT

A system for viral monitoring in effluent includes at least one graphene-based field-effect transistor and circuitry, wherein the circuitry is configured to repeatedly monitor and determine presence of SARS-CoV-2 (COVID virus) in the effluent. The circuitry is configured to apply a gate voltage and measure a conductance across each of the at least one graphene-based field-effect transistor, compare the measured conductance across each of the at least one graphene-based field-effect transistor to a threshold conductance, and determine whether levels of the COVID virus exceed a predetermined threshold in the effluent. If levels of the COVID virus exceed the predetermined threshold in the effluent, the circuitry is configured to remove at least a portion of the bound COVID virus from the proteins of the at least one graphene-based field-effect transistor.

14 Claims, 11 Drawing Sheets

(56) References Cited

U.S. PATENT DOCUMENTS

| | | | | |
|---|---|---|---|---|
| 2002/0044954 | A1* | 4/2002 | Duncan | A01N 37/34 |
| | | | | 424/409 |
| 2005/0224346 | A1 | 10/2005 | Holm-Kennedy | |
| 2006/0055392 | A1 | 3/2006 | Passmore et al. | |
| 2012/0168784 | A1* | 7/2012 | Fife | G01N 27/4145 |
| | | | | 257/E33.012 |
| 2013/0089932 | A1* | 4/2013 | Wu | G01N 33/5438 |
| | | | | 257/253 |
| 2016/0245777 | A1* | 8/2016 | Kawahara | G01N 27/4145 |
| 2019/0033252 | A1* | 1/2019 | Huang | H10N 30/2047 |
| 2019/0178837 | A1 | 6/2019 | Xu et al. | |
| 2019/0262827 | A1 | 8/2019 | Lalonde et al. | |
| 2020/0132622 | A1* | 4/2020 | Rothberg | G01N 27/4148 |

FOREIGN PATENT DOCUMENTS

| | | | |
|---|---|---|---|
| JP | 2013-544347 | A | 12/2013 |
| JP | 2019-525200 | A | 9/2019 |
| JP | 2020-046284 | A | 3/2020 |
| WO | WO 03/052097 | A1 | 6/2003 |
| WO | WO 2016/019381 | A1 | 2/2016 |
| WO | WO 2018/053932 | A1 | 3/2018 |
| WO | WO 2020/116012 | A1 | 6/2020 |

OTHER PUBLICATIONS

Bulyha et al. 'Bio-sensors: Modelling and Simulation of Biologically Sensitive Field-Effect Transistors,' ERCIM News, No. 85, Apr. 2011 (Year: 2011).*

Gilbride et al. (Molecular techniques in wastewater . . . , Journal of Microbiological Methods, vol. 66, pp. 1-20, Apr. 24, 2006 (Year: 2006).*

Xiaoyan Zhang et al.; "Electrical probing of COVID-19 spike protein receptor binding domain via a graphene field-effect transistor"; Cornell University; Mar. 27, 2020; 20 pages.

Giwan Seo et al.; "Rapid Detection of COVID-19 Causative Virus (SARS-CoV-2) in Human Nasopharyngeal Swab Specimens Using Field-Effect Transistor Based Biosensor"; ACS Publications; Apr. 15, 2020; 8 pages https://dx.doi.org/10.1021/acsnano.0c02823.

M. Kitajima et al.; "SARS-CoV-2 in wastewater: State of the knowledge and research needs", Science of the Total Environment 739 (2020) 139076, www.elsevier.com/locate/scitoteny, 19 pages.

Neel V. Patel; "Antigen testing could be a faster, cheaper way to diagnose covid-19," MIT Technology Review, Apr. 24, 2020, 6 pages https://www.technologyreview.com/2020/04/24/1000486.

Hokkaido University, "Using wastewater to monitor COVID-19," Medical Xpress, May 25, 2020, 3 pages https://medicalxpress.com/new/2020-05-wastewater-covid-.html.

Sharon Begley, "Wastewater testing gains traction as a Covid 19 early warning system," STAT, May 28, 2020, 7 pages.

Jesus de La Fuente, "Lets Leam," Graphenea, 6 pages.

Miklos Bolza, "Lets Learn," Graphenea, 8 pages.

Graphene FET chip S10 | Sigma=Aldrich https://www.sigmaaldrich.com/catalog/product/aldrich/grfets10?lang=en&region=US, 6 pages.

Rhiannan Forsyth et al.; "Graphene Field Effect Transistors for Biomedical Applications: Current Status and Future Prospects," Centre for Nanohealth, College of Engineering, Swansea University, Diagnostics 2017, 18 pages.

Yu-Cheng Suy et al., "Review-Filed-Effect Transistor Biosensing: Devices and Clinical Application," Graduate Institute of Electronics Engineering, National Taiwan University, Taipei, Taiwan, ECS Journal of Solid State Science and Technology, 7 (7) Q3196-Q3207 (2018), 13 pages.

Wangyang Fu, et al.; "Sensing at the Surface of Graphene Filed-Effect Transistors," Advanced Science News, Advanced Materials, 2017, 25 pages.

G. Giovannetti, et al.; "Doping Graphene with Metal Contacts," Physical Review Letters 101, 026803 (2008), Jul. 11, 2008, 4 pages.

Guangfu Wu,et al.; "Doping effects of surface functionalization on graphene with aromatic molecule and organic solvents," Applied Surface Science, vol. 425, Dec. 15, 2017, pp. 713-721, 4 pages.

W. Fu et al.; "High mobility graphene ion-sensitive field-effect transistors by noncovalent functionalization," Nanoscale, 2013, 5, 12104-12110, www.rsc.org/nanoscale, 7 pages.

Savannah Afsahi et al,; "Novel graphene-based biosensor for early detection of Zika virus infection," Biosensor and Bioelectronics 100 2018) 85-88, www.elsevier.com locate/bios, 4 pages.

Yasushi Kanai et al.; "Graphene Filed Effect Transistor-Based Immunosensor for Ultrasensitive Noncompetitive Detection of Small Antigens," America Chemical Society, ACS Sens. 2020, 5, 24-28, 5 pages.

Deana Kwong Hong Tsang, et al.; "Chemically Functionalized Graphene FET Biosensor for the Label-free Sensing of Exosomes," Scientific Reports | (2019) 9:13946 | https:/doi org/10.1038/s41598-019-50412-9. www.nature.com/scientificreports, 10 pages.

Lakshmanane Premkumar, et al.; "The receptor-binding domain of the viral spike protein is an immunodominant and highly specific target of antibodies in SARS-CoV-2 patients," Science Immunology | Research Article, Sci. Immunol. 5, eabc8413 (2020), Jun. 11, 2020, 9 pages.

Michael Taeyoung Hwang, et al.; "Ultrasensitive detection of nucleic acids using deformed graphene channel field effect biosensors," Nature Communications | (2020)11:1543 | https://doi.org/10.1038/s41467-020-15330-9 | www.nature.com/naturecommunications, 11 pages.

Yasuhide Ohno, et al.; "Label-Free Biosensors Based on Aptamer-Modified Graphene Field-Effect Transistors," Journal of the American Chemical Society, Jul. 21, 2020, 33 pages https://pubs.acs.org/doi/pdf/10.1021/ja108127r#.

Jul. 21, 2020; Graphene FET Biosensing—Google Scholar, https://scholar.google.com/scholar?hl=en@as_sdt=0%2C6&α=Graphene+FET+Biosensign&og= 2 pages.

Extended European Search Report issued Oct. 21, 2024 in European Patent Application No. 21880765.9, 11 pages.

Chinese Office Action dated Sep. 4. 2025, issued in Chinese Application No. 202180072262.7 (With English translation).

European Communication pursuant to Article 94(3) EPC issued Jul. 2, 2025, in corresponding European Patent Application No. 21 880 765.9, 6 pages.

Japanese Office Action daled Jul. 29, 2026, issued in Japanese Patent Application No. 2023-622898 (with English translation).

* cited by examiner

450

551 — RECEIVE CURRENT FROM TRANSISTOR(S)

552 — CALCULATE CONDUCTANCE OF TRANSISTOR(S)

553 — COMPARE CONDUCTANCE OF TRANSISTOR(S) TO CONDUCTANCE THRESHOLD

554 — PERFORM GLOBAL COMPARISON TO RESPONSE THRESHOLD

555 — DETERMINE DEVICE STATUS BASED ON COMPARISONS

665

DETERMINE DEVICE STATUS

450

+

REVERSE GATE POLARITY TO DETACH ANTIGEN FROM CAPTURE PROTEIN

667

RINSE GRAPHENE SURFACE WITH BUFFER TO DETACH ANTIGEN FROM CAPTURE PROTEIN

666

SYSTEM, APPARATUS, AND METHOD FOR VIRAL MONITORING IN EFFLUENT

CROSS-REFERENCE TO RELATED APPLICATIONS

The present application is a continuation Application of U.S. application Ser. No. 17/070,308, filed Oct. 14, 2020, the entire content of each of these applications is incorporated by reference herein in its entirety for all purposes.

BACKGROUND

Field of the Disclosure

The present disclosure relates to continuous monitoring of fluid bodies for detecting hazardous viral loads in the environment.

Description of the Related Art

Rapid and accurate identification and characterization of a potential pathogen is crucial for disease control and the prevention of epidemics stemming from emerging infectious diseases.

Coronavirus disease 2019 (COVID-19) is a newly emerged human infectious disease associated with severe respiratory distress. In December 2019, a series of cases of pneumonia of unknown cause were reported in Wuhan in the Hubei province of China. Later, the 2019 novel coronavirus was identified from the bronchoalveolar lavage fluid of a patient and it was subsequently renamed severe acute respiratory syndrome coronavirus 2 (SARS-CoV-2) by the International Committee on Taxonomy of Viruses. As human-to-human transmission rapidly increased, the World Health Organization classified the COVID-19 outbreak as a pandemic on Mar. 12, 2020. Coronaviruses (CoVs), and SARS-CoV-2, in particular, cause mild to moderate upper respiratory tract illnesses in both humans and animals. Because no specific drugs or vaccines are yet available for COVID-19, the development of highly sensitive and rapid biosensing devices has become increasingly important for early diagnosis, management of potential contacts, and containment of outbreaks.

Both viable SARS-CoV-2 and viral RNA are shed in bodily excreta, including saliva, sputum, and feces, which are subsequently disposed of in wastewater. Although it is believed that the major transmission route of this virus is inhalation via person-to-person aerosol/droplet transmission and fomite to hand contamination, currently available evidence indicates the need for better understanding of the role of wastewater as a potential source of epidemiological data and as a factor in public health risks. In fact, recent findings suggest the presence of SARS-CoV-2 RNA in wastewater provides an opportunity to use wastewater as a surveillance tool for the invasion, prevalence, molecular epidemiology, and potential eradication of the virus in a community.

Surveillance of wastewater, however, has often focused on the implementation of bench-top testing devices and intricate biological assays requiring removal of a wastewater sample from effluent and transport of the sample to a testing facility. Moreover, these available testing methods there are expensive, time-consuming, and require specialized personnel. Thus, a need exist for solutions to wastewater surveillance that provide continuous monitoring in the field and eliminate the need to obtain samples in what may be an overly burdensome and expensive manner. A process that can be further applicable to a range of infectious agents is desirable.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to monitoring of viral loads in effluent.

According to an embodiment, the present disclosure further relates to a system for viral monitoring in effluent, comprising a biosensor including at least one field-effect transistor along a length of an apparatus, the at least one field-effect transistor having one or more capture proteins conjugated thereto, the one or more capture proteins being configured to bind a virus in the effluent, and a fluidic channel arranged above the at least one field-effect transistor and along the length of the apparatus such that fluid of the effluent flows over the at least one field-effect transistor via the fluidic channel, and processing circuitry configured to apply a gate voltage to each of the at least one field-effect transistor, measure a conductance across each of the at least one field-effect transistor, a change in the conductance being based on an amount of the virus bound to the one or more capture proteins, compare the measured conductance across each of the at least one field-effect transistor to a threshold conductance, and transmit, to a computing device and when the comparison indicates the measured conductance across each of the at least one field-effect transistor satisfies the threshold conductance, information indicating a presence of the virus in the effluent, wherein the at least one field-effect transistor is a graphene-based field-effect transistor and the one or more capture proteins are SARS-CoV-2 spike antibodies.

According to an embodiment, the present disclosure further relates to an apparatus for monitoring of viral load in effluent, comprising processing circuitry configured to apply a gate voltage to each of at least one field-effect transistor disposed along a length of an apparatus, the at least one field-effect transistor having one or more capture proteins conjugated thereto, the one or more capture proteins being configured to bind a virus (or its breakdown product) in the effluent, measure a conductance across each of the at least one field-effect transistor, a change in the conductance being based on an amount of the virus bound to the one or more capture proteins, compare the measured conductance across each of the at least one field-effect transistor to a threshold conductance, and transmit, to a computing device and when the comparison indicates the measured conductance across each of the at least one field-effect transistor satisfies the threshold conductance, information indicating a presence of the virus or breakdown product in the effluent, wherein the gate voltage is applied to a fluidic channel arranged above the at least one field-effect transistor and along the length of the apparatus such that fluid of the effluent flows over the at least one field-effect transistor via the fluidic channel, the at least one field-effect transistor is a graphene-based field-effect transistor, and the one or more capture proteins are SARS-CoV-2 spike antibodies.

According to an embodiment, the present disclosure further relates to a method for monitoring of viral load in effluent, comprising applying, by processing circuitry, a gate voltage to each of at least one graphene-based field-effect transistor disposed along a length of an apparatus, the at least one graphene-based field-effect transistor having one or more capture proteins conjugated thereto, the one or more capture proteins being configured to bind a virus in the effluent, measuring, by the processing circuitry, a conductance across each of the at least one graphene-based field-effect transistor, a change in the conductance being based on an amount of the virus bound to the one or more capture proteins, comparing, by the processing circuitry, the measured conductance across each of the at least one graphene-based field-effect transistor to a threshold conductance, and transmitting, by the processing circuitry to a computing device, information indicating a presence of the virus in the effluent to a computing device when the comparing indicates the measured conductance across each of the at least one graphene-based field-effect transistor satisfies the threshold conductance, wherein the one or more capture proteins are one or more SARS-CoV-2 spike antibodies.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
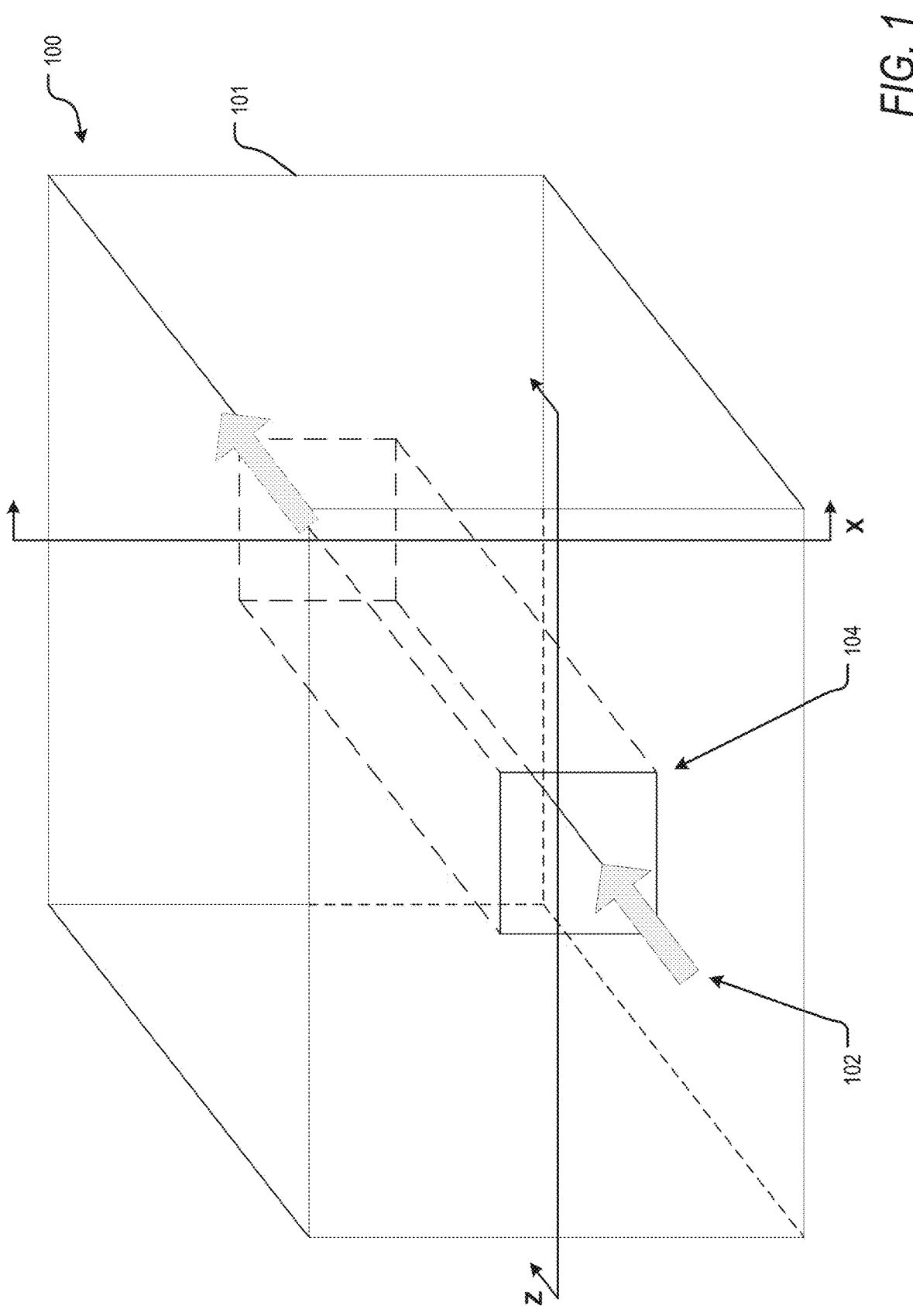
FIG. 1 is a perspective schematic of a device for monitoring viral loads in effluent, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The progression of the COVID-19 pandemic has been monitored primarily by testing symptomatic individuals for the presence of SARS-CoV-2 RNA and counting the number of positive tests over time. However, in the United States and other countries, the spread of COVID-19 has commonly exceeded the testing capacity of public health systems. Moreover, test results are a lagging indicator of the pandemic's progression, because testing is usually prompted by symptoms, which may take 2 weeks to present after infection, and delays occur between the appearance of symptoms, testing, and the reporting of test results.

Monitoring sewage in a community's collection or treatment system has been used previously to provide early surveillance of disease prevalence at a population-wide level, notably for polio, and might be similarly beneficial for the current COVID-19 pandemic. In sewage, SARS-CoV-2 virus and fragments, although largely non-infective, have been found to be present and may serve as a marker of infection hotspots and be reflective of the recovery from the pandemic state. To this end, SARS-CoV-2 RNA is present in the stool of patients with COVID-19 and in raw wastewater, and increased RNA concentrations in raw wastewater have been recently associated with increases in reported COVID-19 cases.

However, the methodologies for testing the presence of SARS-CoV-2 RNA have been limited to those traditionally used for clinical specimens, including molecular testing (e.g. polymerase chain reaction nucleic acid amplification), viral antigen testing (e.g. flu-like readout testing), and antibody titer testing to determine acquired immunity. These tests can be expensive, require specialized equipment and manpower, and specialized labs, a sequence of rate-limiting steps that generally limit the ability to report results quickly.

Moreover, the utility of wastewater SARS-CoV-2 concentrations for tracking the progression of COVID-19 infections in communities is poorly understood. For instance, there is often a delay between when infections occur, when SARS-CoV-2 concentrations appear in the wastewater, and when positive test results identifying the infections are performed.

What is understood, though, is an appreciation of the possible benefits of continuous sample collection that, under current testing methodologies, are not achievable due to impracticable burdens to field scientists and other researchers. As a result, the present disclosure describes a device for continuous monitoring of the presence of SARS-CoV-2 RNA in wastewater, or effluent, and the immediate communication of those results to a response center for evaluation of the data and consideration of its impacts on public health policy.

In other words, the present disclosure describes a device that provides automatic testing not requiring sampling or human intervention in a way that is inexpensive and able to continuously monitor for the presence of the virus or its breakdown products.

To this end, the present disclosure describes a device including field-effect transistor circuitry that can be adapted to bind, and thereby detect, a SARS-CoV-2 antigen(s). Among the many diagnostic methods currently available, field-effect transistor-based biosensing devices have several advantages, including the ability to make highly sensitive and instantaneous measurements using small amounts of analytes or antigens. Field-effect transistor-based biosensors are considered to be potentially useful in clinical diagnosis, point-of-care testing, and on-site detection. In an embodiment, the present disclosure describes a device including a graphene-based field-effect transistor. Graphene is a two-dimensional sheet of hexagonally arranged carbon atoms, all of which are exposed on its surface. Graphene has proven to be a useful material for various sensing platforms due to its extraordinary properties, including high electronic conductivity, high carrier mobility, and large specific area. Graphene-based field-effect transistor biosensors can detect surrounding changes on their surface and provide an optimal sensing environment for ultrasensitive and low-noise detection. From this standpoint, graphene-based field-effect transistor technology is very attractive for applications related to sensitive immunological diagnosis.

As in the present disclosure, a graphene-based field-effect transistor-based device can be used to detect the presence of SARS-CoV-2 in sewage wastewater, or effluent. The effluent may be flowed over a sensing surface of the graphene-based field-effect transistor. Upon binding of the SARS-CoV-2 antigen to biomolecules conjugated to the sensing surface of the graphene-based field-effect transistor, a conductance of the graphene-based field-effect transistor changes and an amount of bound antigen can be quantified. Considered instantly, the changes in conductance indicate the presence or absence of virus in the wastewater. Considered over time, an increasing conductance shows a developing or growing infection hotspot, as binding of the SARS-CoV-2 antigen increases conductance of the graphene-based field-effect transistor. Conversely, a decreasing conductance with time shows a reduction of the infection rate.

SARS-CoV-2, a betacoronavirus, has a single-positive strand RNA genome. CoV genomes encode four structural proteins: spike, envelope, matrix, and nucleocapsid. Although the viral pathogenesis of SARS-CoV-2 is unknown, recent studies reported that SARS-CoV-2 uses angiotensin-converting enzyme II (ACE2) as a cellular entry receptor, ACE2 also being a well-known host cell receptor for SARS-CoV. SARS-CoV-2 colocalizes with ACE2 in animal cells, and its spike protein binds ACE2 with high affinity.

According to an embodiment, the graphene-based field-effect transistor may be functionalized by conjugation of capture protein to a sensing surface of the graphene. The capture protein may be an antibody and may be designed to bind to a SARS-CoV-2 fragment such as a spike protein or receptor binding domain, also known as an ACE2 receptor. Thus, as in the present disclosure, the spike protein capture antibody may be conjugated to the sensing surface of the graphene by methods outlined below. For simplicity, binding between the SARS-CoV-2 fragment, or SARS-CoV-2 spike protein, and the capture protein, or spike protein capture antibody, may be referred to herein, generally, as virus binding, bound virus, and the like.

According to an embodiment, the device may include a power source, an ammeter, or similar method to measure conductivity across the graphene-based field-effect transistor, a comparator, or similar method to calculate changes in conductance, and a telemetry unit, or similar method for transmitting a data signal from the device to a remote monitoring station, response center, or mobile device.

In an embodiment, all components of the device except for a fluidic channel through which effluent will flow will be covered with an impervious layer such as a silastic to prevent seepage of water into the device. The device may be designed to be inserted, for instance, into an effluent line from a sewage treatment facility to allow for continuous monitoring and identification of potential environment 'hot spots'.

In an embodiment, the device includes methods for removing bound antigen(s) from the capture protein(s). In one instance, a buffer washing system may be included as a component of the device. In another instance, a gate polarity reversing method can be implemented to drive bound antigen(s) from the capture protein(s).

In this way, the device and methods of the present disclosure enable continuous, real-time, automatic, inexpensive monitoring of virus particles in sewage without needing transportation of samples, laboratories, or personnel. While especially applicable to the COVID-19 pandemic, it could easily be adapted to other infectious agents or organic substances indicative of health or disease. Such a unit could also be used as an instantaneous, point of care, clinical test for virus presence or presence of antibodies in bodily fluid specimens.

Referring now to the Figures, FIG. 1 is a perspective schematic of an apparatus for monitoring viral loads in effluent, according to an exemplary embodiment of the present disclosure. The apparatus may be referred to herein as a viral load monitoring device (VLMD).

As in FIG. 1, a VLMD 100 may be a device having a housing 101. The housing 101 may be configured to hold a biosensor, processing circuitry, a power source, a buffer reservoir, a wireless communication unit, and the like, as will be described further with reference to FIG. 2. The housing 101 of the VLMD 100 may be designed such that fluid flow 102 may travel therethrough via a fluidic channel 104. The fluidic channel 104 may be a component of a biosensor or a component of the housing 101 of the VLMD 100. Nevertheless, the fluidic channel 104 may be arranged such that fluid flow 102 of effluent travels over a sensing surface of a graphene-based field-effect transistor of the biosensor.

Though presented as being of a rectangular shape in FIG. 1, it can be appreciated that the housing 101 of the VLMD 100 may be of any design that allows for effluent to be brought into proximity with the biosensor and provides sufficient structure to house, for instance, the components described above.

In an embodiment, dimensions of the housing 101 of the VLMD 100 may be governed by a design of the biosensor and size and shape of attendant circuitry and other requisite components. For instance, a z-dimension of the housing 101 of the VLMD 100 may be lengthened in order to accommodate an increasing number of graphene-based field-effect transistors within the biosensor, assuming the graphene-based field-effect transistors are arranged along the z-dimension. Similarly, an x-dimension of the housing 101 of the VLMD 100 may be lengthened in order to accommodate an x-dimension of each graphene-based field-effect transistor of each biosensor. Moreover, a y-dimension of the housing 101 of the VLMD 100 may be adjusted in order to accommodate a predetermined volume of fluid of the effluent above the sensing surface of each graphene-based field effect transistor, the y-dimension being determined in coordination with the x-dimension.

Figure 2:
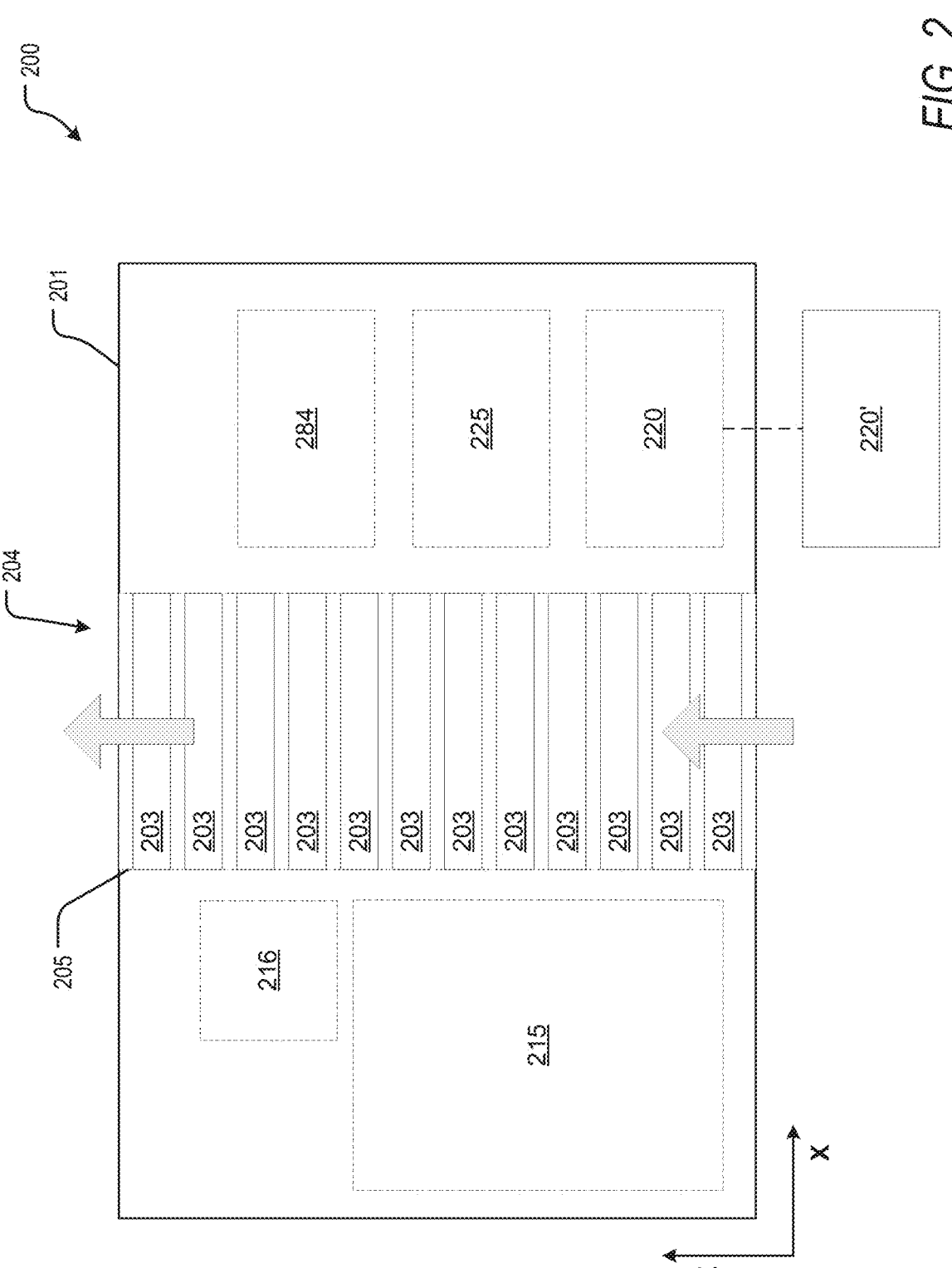
FIG. 2 is a cross-sectional schematic of a device for monitoring viral loads in effluent, according to an exemplary embodiment of the present disclosure.

In order to discuss further the internal components of the VLMD 100, FIG. 2 provides a cross-sectional schematic, according to an exemplary embodiment of the present disclosure. It can be appreciated that the cross-sectional schematic provides a view of a VLMD 200 along the x-dimension and the dashed lines indicate components that are located within a housing 201 of the VLMD 200.

According to an embodiment, the VLMD 200 of FIG. 2 includes the housing 201 and the fluidic channel 204 through which fluid of the effluent, represented by the large, hued arrows, flows. Components that may be arranged, as functionally-appropriate, within the housing 201 include a biosensor 205, controller 220, a power supply 225, a wireless communication unit 284, a buffer reservoir 215, and a pump 216. The controller 220 may include processing circuitry configured to control the above-components of the VLMD 200. In an embodiment, the controller 220 may include component-specific controllers, as will be described with respect to FIG. 7.

In an embodiment, and as indicated by the solid box, the controller 220 may be a controller 220' that is remotely located. In such an embodiment, the controller 220' may be wired or wireless. The controller 220 may be in electrical communication with each of the power supply 225, the wireless communication network 284, the biosensor 205, and the pump 216. The buffer reservoir 215 may contain buffer solution that can be supplied to the fluidic channel 204 of the VLMD 200 by the pump 216. Such introduction of the buffer solution to the fluidic channel 204 can be initiated in response to determining that a threshold amount of antigen is detected by the biosensor 205, the buffer solution thereby removing bound antigen from the biosensor 205 such that additional cycles of measurements can be performed.

As can be appreciated from FIG. 2, the biosensor 205 may include one or more graphene-based field-effect transistors (GFET) 203. Each of the one or more GFETs 203 can be arranged along the z-dimension of the housing 201 of the VLMD 200. Fabrication of the one or more GFETs 203 will be described in greater detail with reference to FIG. 3B.

FIG. 3A through FIG. 3D provide additional description of the VLMD of the present disclosure, with specific reference to a biosensor thereof.

Figure 3A:
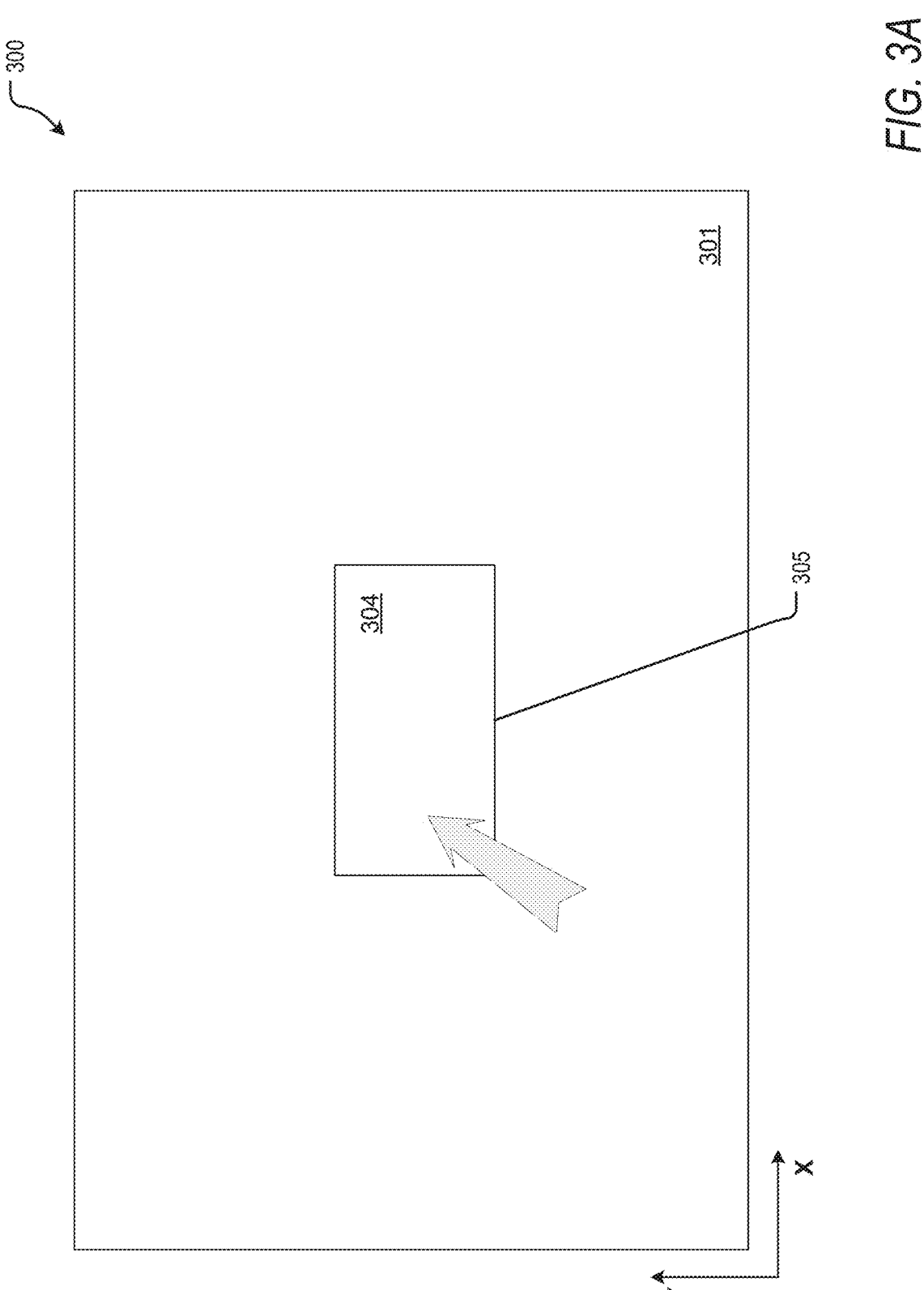
FIG. 3A is a cross-sectional schematic of a device for monitoring viral loads in effluent, according to an exemplary embodiment of the present disclosure.

Initially, with reference to FIG. 3A, a cross-sectional schematic of an apparatus for monitoring viral loads in effluent is provided, according to an exemplary embodiment of the present disclosure. It can be appreciated that the cross-sectional schematic provides a view of a VLMD 300 along the y-dimension. According to an embodiment, the VLMD 300 of FIG. 3A includes the housing 301 and the fluidic channel 304 proximate a biosensor 305, fluid of the effluent, indicated by the tapered, hued arrow, flowing through the fluidic channel 204 and over a sensing surface of a GFET of the biosensor 305.

Figure 3B:
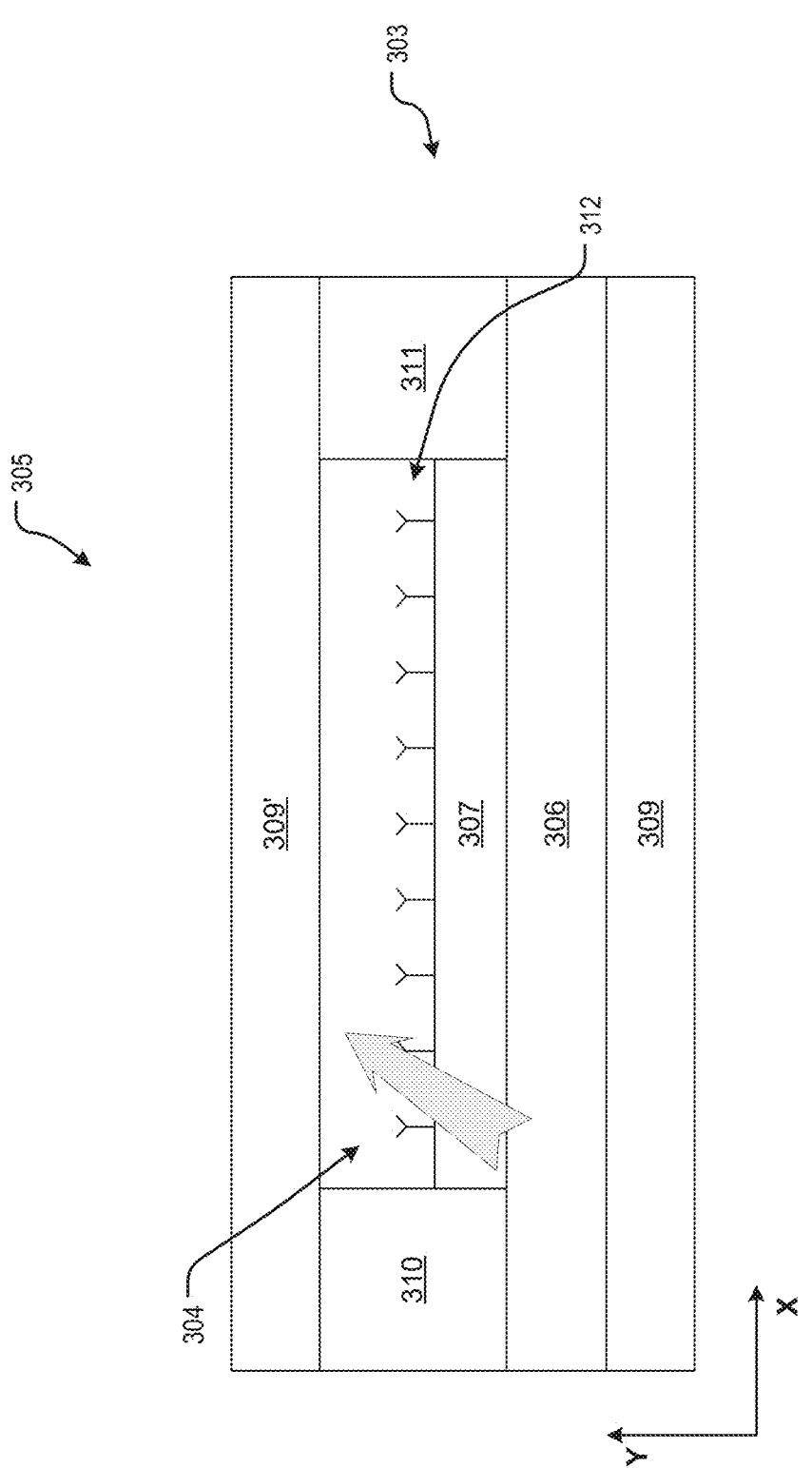
FIG. 3B is a cross-sectional schematic of a device for monitoring viral loads in effluent, according to an exemplary embodiment of the present disclosure.

With reference to FIG. 3B, an enlargement of the biosensor 305 of the VLMD 300 of FIG. 3A is described. Though it can be appreciated that the biosensor 305 of the VLMD may comprise one or more GFETs, as shown in FIG. 2, description of the biosensor 305 will be made with reference to a single GFET 303, for simplicity.

Electrical detection of biomolecules using nanomaterials can often achieve high sensitivity because nanomaterials are extremely sensitive to electronic perturbations in the surrounding environment. Graphene, a single layer of carbon atoms in a two-dimensional honeycomb lattice, has potential applications in the electrical detection of biological species due to their unique physical properties. Graphene-based sheets are flat and large in lateral dimensions, which make it easier for device fabrication (e.g., making electrical contact with electrodes) than carbon nanotubes (CNTs), for instance. Compared to CNTs, graphene-based sheets have a higher carrier mobility and specific surface area, which enhances the sensor performance.

According to an embodiment, the present disclosure describes a biosensor including at least one GFET having linker-biomolecule conjugates immobilized thereto. For brevity, the biosensor including the at least one GFET may be referred to herein, interchangeably, as a GFET-based biosensor. Referring to FIG. 3B, a GFET-based biosensor 305 includes, as components of a GFET 303, a substrate 309 having a passivation layer 306, a source electrode 310 and a drain electrode 311 each disposed on one surface of the substrate 309, and a graphene-based sheet 307 configured to be a conducting channel suspended above the substrate 309 and to electrically connect the source electrode 310 and the drain electrode 311. The graphene-based sheet 307 may be decorated with linker-biomolecule conjugates 312, which anchor biomolecules to the surface of the graphene-based sheet 307. The linker-biomolecule conjugates 312 may comprise 1-pyrenebutryic acid N-hydroxysuccinimide ester (PBASE) conjugated with capture antibodies, for instance. The capture antibodies function as the specific recognition group for the target biomolecule, which will be discussed with reference to FIG. 3C and FIG. 3D. In an embodiment, the GFET-based biosensor 305 may include an additional substrate 309', which serves to form an upper surface a fluidic channel 304 of the GFET-based biosensor 305.

In some embodiments, the source electrode 310 and the drain electrode 311 may be formed of any material having electrical conductivity. Examples include, but are not limited to, gold (Au), platinum (Pt), chromium (Cr), palladium (Pd), or combinations thereof. In some embodiments, the substrate 309 and the additional substrate 309' may include silicon (Si), silicon dioxide ($SiO_2$), aluminum oxide, sapphire, germanium, gallium arsenide, an alloy of silicon and germanium, or indium phosphide. An exemplary substrate 309, 309' includes a Si wafer. In some embodiments, the passivation layer 306 may include aluminum, zinc, titanium, Si, or an oxide or nitride thereof, or a synthetic resin such as, but are not limited to, polymethyl methacrylate, polyester, polystyrene, polyethylene terephthalate, polycarbonate, polyvinylidene chloride or triacetate. An exemplary passivation layer 306 includes a $SiO_2$.

In some embodiments, the biomolecule conjugated to the linker may include a protein, nucleic acid molecule, microorganism, and a low molecular weight organic compound. Examples include, but are not limited to, an immune protein, an antigen, an enzyme, a nonimmune protein, an immunoglobulin-binding protein, a sugar-binding protein, a sugar chain recognizing sugar, fatty acid or fatty acid ester, a ligand, an aptamer, and polypeptide or oligopeptide having ligand-binding ability. Examples of an immune protein may include an antibody whose antigen is a target biomolecule. In an example, such antibodies may include various immunoglobulins such as IgG, IgM, IgA, IgE or IgD. In a particular example, such antibodies include an anti-SARS-CoV-2 spike protein antibody which can be conjugated to the linker and used to detect the target biomolecule, SARS-CoV-2 virus.

According to an embodiment, and as it relates to SARS-CoV-2 virus, the GFET of the GFET-based biosensor 305 of FIG. 3B may be manufactured according to the below with reference to FIG. 3C.

In an embodiment, graphene may be transferred to a SiO₂/Si substrate using conventional wet-transfer methods. Poly(methyl methacrylate) (PMMA) may be spin-coated at 500 rpm for 10 seconds and at 3000 rpm for 30 seconds onto graphene on copper foil. PMMA/graphene on copper foil may be etched in copper etchant. After etching of the copper foil, the PMMA/graphene layers may be moved using clean glass slides into a deionized (DI) water bath, and the copper etchant may be washed away. Subsequently, the PMMA/graphene layer may be transferred to a SiO₂/Si substrate and dried under ambient conditions overnight. The PMMA layer may be removed in an acetone bath for 2 hours. Finally, the graphene can be transferred onto the substrate, followed by isopropyl alcohol washing and drying under a stream of nitrogen gas. To fabricate practical graphene-based devices, the transferred graphene can be patterned into linear shapes by photolithography and etched by a reactive ion-etching method. To generate, for instance, a Au/Cr electrode layer on the etched graphene layer, metallization was performed using a thermal evaporation method and a lift-off technique. The dimensions of a sensing surface of the GFET can be 100×100 μm² (L×W), in an example.

According to an embodiment, and having fabricated the GFET, the GFET may be functionalized by a linker-biomolecule conjugate in order to sense aspects of the SARS-CoV-2 virus. In order to immobilize a SARS-CoV-2 antibody as the biomolecule, or capture protein, on the sensing surface of the graphene, the fabricated GFET can be first soaked in, as the linker, 2 mM PBASE in methanol for 1 hour at room temperature and then rinsed several times with phosphate buffered saline (PBS) and DI water. Finally, the functionalized GFET can be exposed to, as the biomolecule, or capture protein, 250 μg/mL SARS-CoV-2 spike antibody for 4 hours in order to generate the GFET-based biosensor 305 visualized in FIG. 3B through FIG. 3D.

Figure 3C:
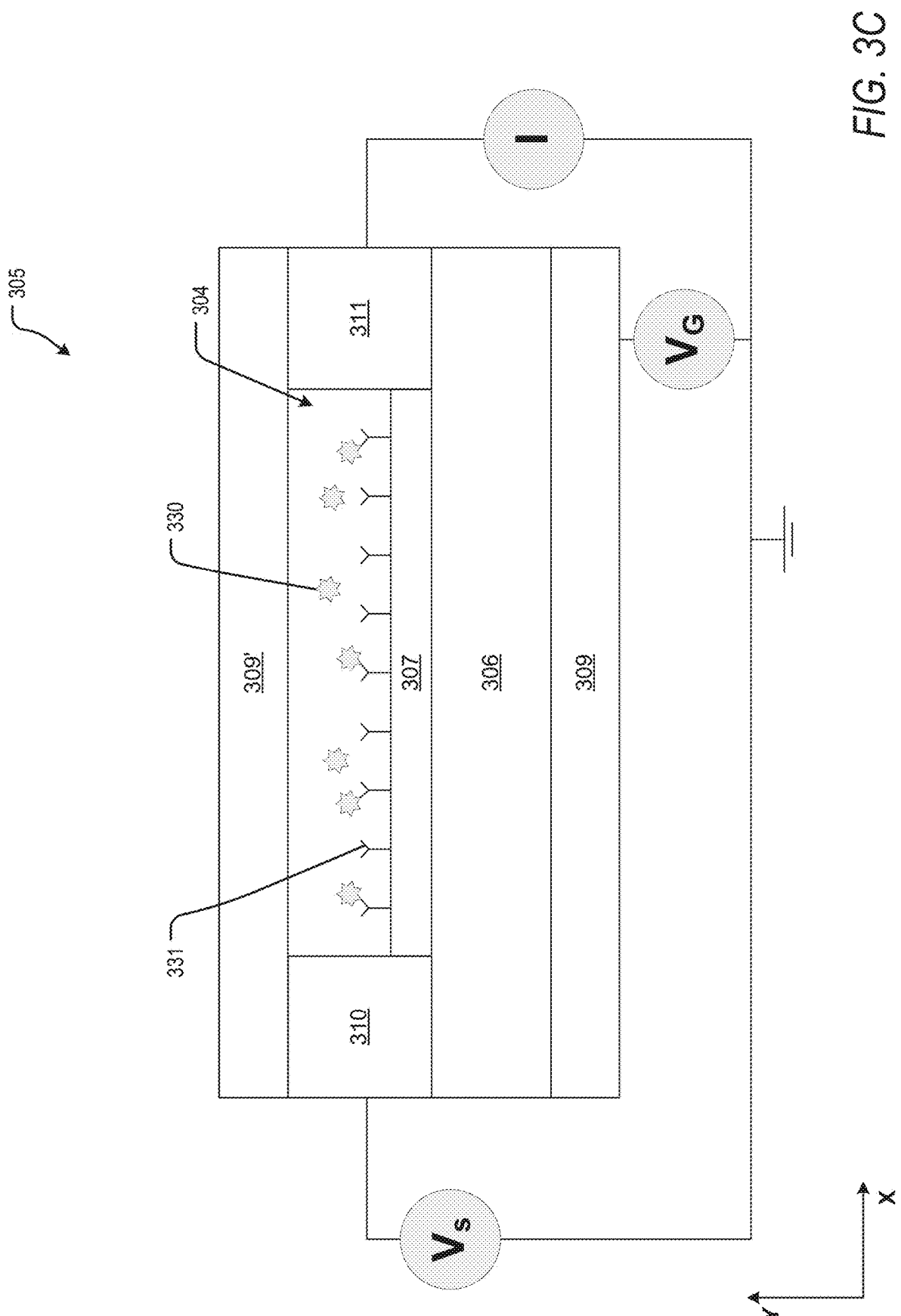
FIG. 3C is a cross-sectional schematic of a device for monitoring viral loads in effluent, according to an exemplary embodiment of the present disclosure.
Figure 3D:
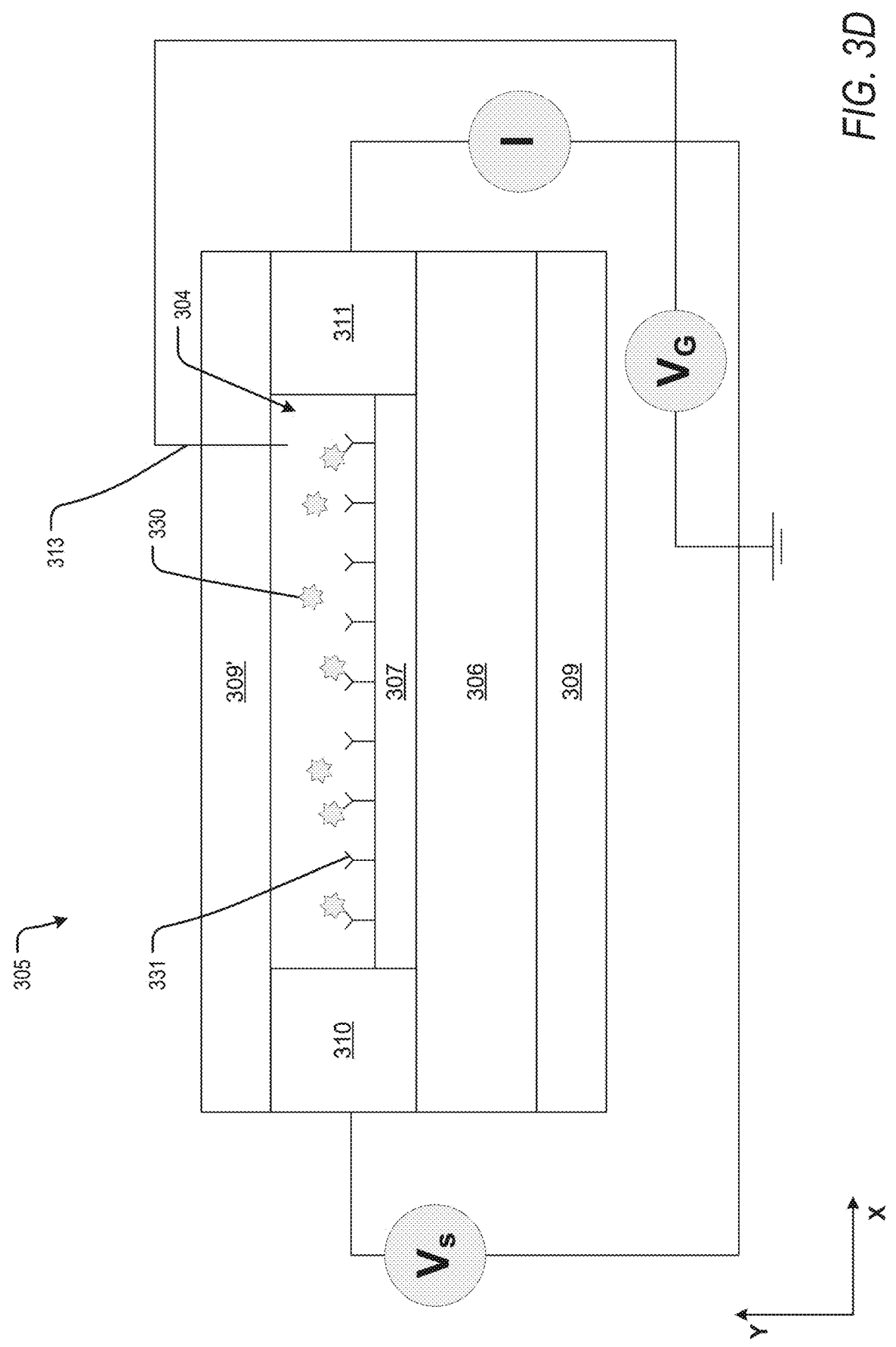
FIG. 3D is a cross-sectional schematic of a device for monitoring viral loads in effluent, according to an exemplary embodiment of the present disclosure.

Referring now to FIG. 3C and FIG. 3D, a cross-sectional schematic of the GFET-based biosensor 305 of FIG. 3B is shown. The GFET-based biosensor 305 of FIG. 3C will be described in context of an application of voltage via a back gate (FIG. 3C) and via a liquid gate (FIG. 3D) and in the presence of target biomolecules, or virus particles.

A typical GFET-based biosensor 305 measurement consists of applying a constant bias voltage ($V_S$) between the source electrode 310 and the drain electrode 311 of a graphene channel 307 and monitoring the resulting source-drain current (I). By changing the gate voltage $V_G$, the electrochemical potential of the charge carriers (i.e., the Fermi energy) can be modulated. As a consequence, the type of charge carriers (which flow in the graphene channel and give the current I) can continuously be tuned from holes to electrons, yielding a so-called "ambipolar behavior".

A change in the electric field can be achieved using the back gate approach of FIG. 3C or the liquid gate approach of FIG. 3D and in combination with binding of the target biomolecules 330 to capture proteins 331 on the sensing surface of the graphene 307. For instance, when the bias voltage ($V_S$) and the gate voltage ($V_G$) are held at fixed voltages, any measured change in current (I) between the drain electrode 311 and the source electrode 310 can be ascribed to target biomolecules 330, or SARS-CoV-2 spike proteins, bound to capture proteins 331, or SARS-CoV-2 spike protein antibodies, conjugated on the sensing surface of the graphene 307 via the linker. In contrast to the back gate geometry of FIG. 3C, FIG. 3D provides a liquid-gated configuration, wherein the gate voltage ($V_G$) is applied to fluid (i.e., effluent) within a fluid channel 304 via a reference electrode 313. The reference electrode 313 is coupled to the graphene 307 through an interfacial capacitance C, consisting of a series of two capacitances, namely the quantum capacitance of graphene ($C_Q$) and the double layer capacitance of the electrolyte ($C_{DL}$). The double layer capacitor is a virtual capacitor formed by the separated charges located at the solid side and the solution side of the interface as described by the Poisson-Boltzmann equation. Liquid-gated GFET biosensors belong to the large family of ion-sensitive FETs. Although the choice of the channel materials, the reference electrode, the operational mode, and the final encapsulation for liquid handling, vary from case to case, the heart of any ion-sensitive FETs lies on the interface between the electrolyte and the solid FET materials.

In view of FIG. 3C and FIG. 3D above, and as in the present disclosure, GFET-based biosensors 305 may be operated at low gate voltages ($V_G$) such that any electrochemical processes and exchange ionic currents are negligible (i.e., the interface is considered to be inert and purely capacitive), although this assumption is not always explicitly stated. Experimental artifacts at moderate or relatively high gate voltages ($V_G$) resulting from such simple assumption are considered mainly of electrochemical nature.

The working principle of a liquid-gated GFET-based biosensor, such as that described with reference to FIG. 3D, is described below. In practice, liquid-gated GFET-based biosensors can be integrated into microfluidic systems, such as the VLMD of the present disclosure, the confinement of the fluidic channel 304 helping to bring target biomolecules 330, or virus particles, to the sensing surface of the graphene 307 and in proximity to the capture proteins 331 attached thereto.

As described generally above, in a typical measurement, receptor molecules, or capture proteins 331, have been immobilized on the sensing surface of the graphene 307 for selective recognition of target biomolecules, or spike proteins of SARS-CoV-2 virus 330. Corresponding I versus $V_G$ curves of such a liquid-gated GFET (FIG. 3D) show similar characteristics as those observed for a back-gated GFET (FIG. 3C). In either the hole regime or in the electron regime, when a positively charged target binds, a depletion of hole carriers (respectively an accumulation of electron carriers) in the graphene 307 occurs due to the field effect. Such doping effect causes a negative shift of the $I(V_G)$.

In a time-dependent measurement, the binding of a positively charged molecule causes a decrease of the current I in the hole regime and an increase of the current I in the electron regime. Conversely, the binding of a negatively charged molecule induces a positive shift of the $I(V_G)$ curve and an increase in the I in the hole regime. In the electron regime—instead—the same event induces a negative shift of the $I(V_G)$ curve and a decrease of the current I. This current modulation in the graphene channel can be expressed as a function of the change in the carrier density $\Delta n$, which is induced by and is proportional to the total number N of charged biomolecules adsorbing on the graphene surface $$-\Delta I = w/l V_{sd} e \mu \Delta n \propto N \tag{1}$$

where w and l are the width and length of the sensing surface of the graphene 307, respectively, e is the electron charge, and μ is the charge carrier mobility. In Equation (1), it is clear that the sensing response, or conductance, of a GFET-based biosensor 305 should be proportional to the total number of adsorbed biomolecules N 330. The quantitative monitoring of biomolecules 330, however, is non-trivial. Challenges lie in characterizing the number of charges each biomolecule 330 carries, in controlling the chemical functionalization, and in identifying the exact sensing reactions at the sensing surface of the graphene 307 in each different regime. To deduce Equation (1), we assume that graphene has a constant carrier mobility μ upon the adsorption of biomolecules 330. This assumption is correct in most cases where the adsorbed biomolecules 330 bind to the receptors 331 and interact weakly with a lattice of the graphene 307.

Nevertheless, as outlined above with respect to Equation (1) and as viewed in context of the SARS-CoV-2 virus, an increase in the number of bound virus particles 330 to the GFET-based biosensor 305 of the present disclosure necessarily results in a proportional increase in the current (I) measured across the source electrode 310 and the drain electrode 311.

During implementation of the VLMD of the present disclosure, the GFET-based biosensor may be provided a bias voltage ($V_{sd}$) of between either of −1000 mV and 0 mV or 0 mV and +1000 mV and a gate voltage ($V_G$) maintained between either of −1000 mV and 0 mV or 0 mV and +1000 mV. In an example, the bias voltage ($V_{sd}$) can be maintained at −100 mV within the VLMD and the gate voltage ($V_G$) may be applied to effluent within the fluidic channel at +100 mV. In an embodiment, the detected electrical response signal, I, can be I or can be normalized as $[\Delta I/I_0]=(I-I_0)/I_0$, where I is the detected real-time current and $I_0$ is the initial current measured across the source electrode and the drain electrode.

Figure 4:
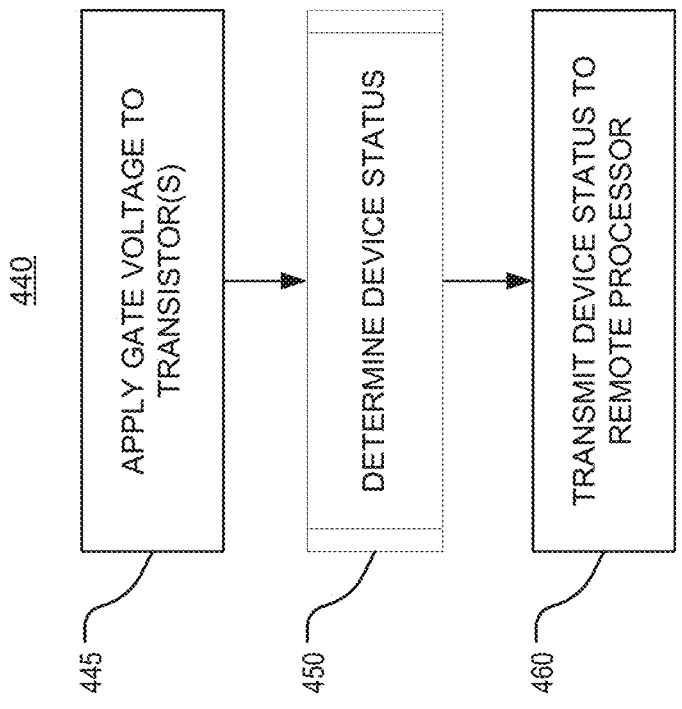
FIG. 4 is a flow diagram of a method for monitoring viral loads in effluent, according to an exemplary embodiment of the present disclosure.

Returning to the Figures, FIG. 4 describes a method for monitoring viral loads in effluent, according to an exemplary embodiment of the present disclosure.

Method 440 of the present disclosure can be performed following deployment of the VLMD to a monitoring site. The monitoring site may be, for instance, a sewage outflow, an outflow of a water treatment facility, and the like. In order to allow the VLMD to be used iteratively, the VLMD can be configured to remove bound virus from the surface of the GFET-based biosensor, thereby enabling the VLMD to remain at the testing site for an extended period of time to provide continuous measurements and viral load monitoring. To this end, the VLMD may transmit data to a monitoring center or response center regarding results of the viral load monitoring. As it relates to longevity in the field, the VLMD may generate a signal when a battery, as a power source of the VLMD, has a stored energy capacity lower than a requisite energy threshold. The VLMD can then be retrieved from the field and replaced.

In an embodiment, the VLMD may include a GFET-based biosensor having one or more GFETs. As a reflection of a realistic implementation, method 440 will be described assuming the VLMD is deployed with a GFET-based biosensor having a plurality of GFETs arranged along the fluidic channel of the VLMD, as shown in FIG. 2.

At step 445 of method 440, a gate voltage may be applied to each GFET of the GFET-based biosensor of the VLMD. In an example, each GFET of the GFET-based biosensor may be a liquid-gated GFET, as described with reference to FIG. 3D. The applied gate voltage may be +100 mV, in an example, and may be provided in order to promote binding of virus in the effluent with SARS-CoV-2 spike protein antibodies (i.e. capture proteins) conjugated to each GFET. It can be appreciated, however, that another gate voltage may be used as appropriate for a specific biosensing objective.

At sub process 450 of method 440, a status of the VLMD can be determined. Determining the current status of the VLMD includes evaluating the conductance of each GFET of the GFET-based biosensor, individually and globally, to determine if sufficient levels of virus are found in the effluent. Sub process 450 of method 440 will be described in greater detail with reference to FIG. 5.

At step 460 of method 440, the current status of the VLMD can be transmitted to a remote processor, monitoring station or the like. The transmission can be performed wirelessly by the wireless communication unit of the VLMD or by a wired transmission, the wired transmission being integrated, for instance, within existing communication infrastructure of the testing environment. The remote processor or the monitoring station may be, in an example, an environmental monitoring agency, epidemiological agency, or other public health group in a position to evaluate the results of the VLMD and provide instructions to proper stakeholders in order to identify potential 'hot spots' and mitigate epidemiological events.

In an embodiment, the transmitted status of the VLMD can be considered instantly or longitudinally based on collected data from a number of transmissions. In this way, and as will be discussed in more detail later, increases or reductions of virus or virus fragments in the effluent can be monitored over time as an indication of upstream infections.

In an embodiment, the transmission at step 460 of method 440 may be a binary indication of a presence of virus relative to a virus detection threshold. In another embodiment, the transmission at step 460 of method 440 may be the binary indication of the presence of the virus relative to the virus detection threshold accompanied by a quantitative measure of the estimated concentration of virus in the effluent. The estimated concentration can be based on a correlation between bound virus and conductance (see Equation (1)), an increasing conductance tracking with an increasing amount of virus being bound to the capture proteins of each GFET of the GFET-based biosensor.

Figure 5:
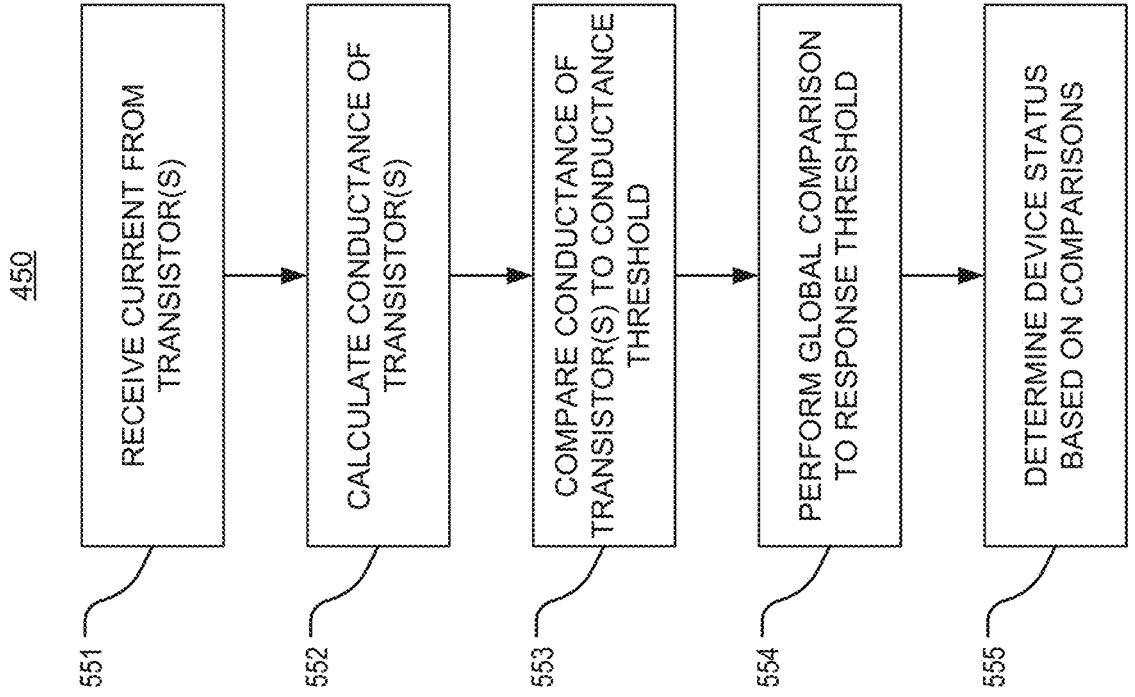
FIG. 5 is a flow diagram of a sub process of a method for monitoring viral loads in effluent, according to an exemplary embodiment of the present disclosure.

Sub process 450 of method 440 will now be further described with reference to FIG. 5. After application of the gate voltage to each GFET at step 445 of method 440, determination of the status of the VLMD begins at step 554 of sub process 450. Step 554 includes receiving a source-drain current from each GFET of the GFET-based biosensor. Based on the source-drain current from each GFET of the GFET-based biosensor, and a respective source-drain voltages applied thereto, a conductance of each GFET of the GFET-based biosensor can be calculated at step 552 of sub process 450.

As indicated above and with reference to Equation (1), the conductance determined for each GFET of the GFET-based biosensor is expected to increase with increasing binding of the virus to the capture proteins conjugated to the surface of each GFET. At step 553 of sub process 450, the calculated conductance for each GFET of the GFET-based biosensor can be compared to a respective conductance threshold. In an example, the respective conductance thresholds for each GFET of the GFET-based biosensor can be based on a concentration of virus within the effluent that defines a virus 'hot spot'. In an embodiment, a viral load composition of the effluent is assumed to be homogenous across the length of the fluidic channel of the VLMD, and so a same conductance threshold can be used for each GFET arranged along the length of the fluidic channel of the VLMD. In another embodiment, it can be assumed that a viral load composition of the effluent is heterogeneous along the length of the fluidic channel that traverses the VLMD, and so different respective conductance thresholds can be applied to each GFET of the GFET-based biosensor. For instance, a conductance threshold for a GFET positioned 'upstream' within the GFET-based biosensor may be higher than a conductance threshold for a GFET positioned 'downstream' within the GFET-based biosensor.

In this way, a global comparison of the responses from each GFET of the GFET-based biosensor can be made at step 554 of sub process 450. In other words, after determining if each GFET does or does not satisfy a respective conductance threshold, it can be determined, globally, if a number of the GFETs of the GFET-based biosensor that satisfied respective conductance thresholds is sufficient to satisfy a global conductance threshold. The global conductance threshold may be, in an example, a simple majority of the plurality of GFETs of the GFET-based biosensor, or may be another number, percentage, or similar metric that sufficiently identifies the presence of the virus in the effluent.

Accordingly, at step 555 of sub process 450, a current status of the VLMD can be determined based on the above comparisons relative to conductance thresholds. Thus, when the number of the GFETs that satisfy respective conductance thresholds satisfies the global conductance threshold, it can be determined that the virus is present in the effluent at levels indicative of a virus 'hot spot'.

Thus, at step 460 of method 440, this determination can be transmitted to, for instance, a response center. When it is determined, as above, that the virus is present in the effluent at levels indicative of a virus 'hot spot', public health professionals can act accordingly to prevent additional spread of the disease at upstream locations. Moreover, the transmission may include, alongside the binary indication and as described above, an estimated concentration of the virus in the effluent. The estimated concentration of the virus in the effluent can be used as an instant- and as a chronological-guide for evaluating the virus in the human population. For instance, if the relative estimated concentration of the virus in the effluent at time t=2 is less than the estimated concentration of the virus in the effluent at time t=1, then it can be reasonably assumed that there are fewer active cases of infection in the upstream communities.

According to an embodiment, and in order to allow for continuous monitoring following binding of the virus to the capture proteins of the GFET-based biosensor, as described above, the present disclosure includes methods for removing bound virus from the capture proteins, as will be described with reference to FIG. 6A and FIG. 6B.

Figure 6A:
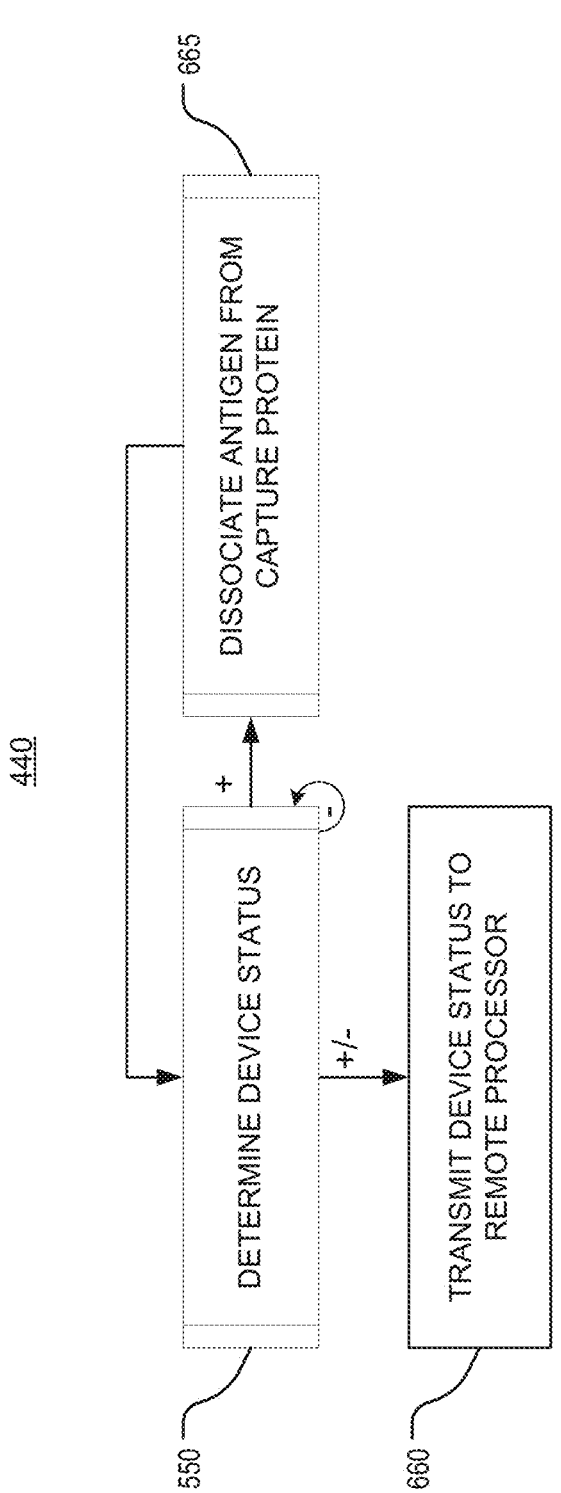
FIG. 6A is a flow diagram of a sub process of a method for monitoring viral loads in effluent, according to an exemplary embodiment of the present disclosure.

With reference to FIG. 6A, method 440 is described with respect to sub process 550 and in view of sub process 665. For instance, if it is determined at sub process 550 that the binary indication of the current status of the VLMD is negative (i.e., no virus is detected in the effluent), method 440 proceeds to step 660 while sub process 550 is repeated. At step 660 of method 440, the negative binary indication of the current status of the VLMD may be transmitted to, for instance, a response center. The transmission may include, as a component of the current status, an estimated concentration of the virus based on the conductance of the GFETs. If, however, it is determined at sub process 550 of method 440 that the binary indication of the current status of the VLMD is positive (i.e. virus is detected at levels considered to be indicative of a virus 'hot spot'), method 440 proceeds, concurrently, to step 660 and to sub process 665. At step 660 of method 440, similar to the above, the positive binary indication of the current status of the VLMD is transmitted to the response center so that proper action may be taken by public health officials. As before, the current status transmission may include an estimated concentration of the virus in the effluent. At the same time, and in order to allow for continued monitoring of the effluent to determine if concentrations of the virus in the effluent increase, decrease, or stabilize over time, sub process 665 of method 440 may be performed to remove at least a portion of the bound virus from the capture proteins of the GFETs of the GFET-based biosensor.

Figure 6B:
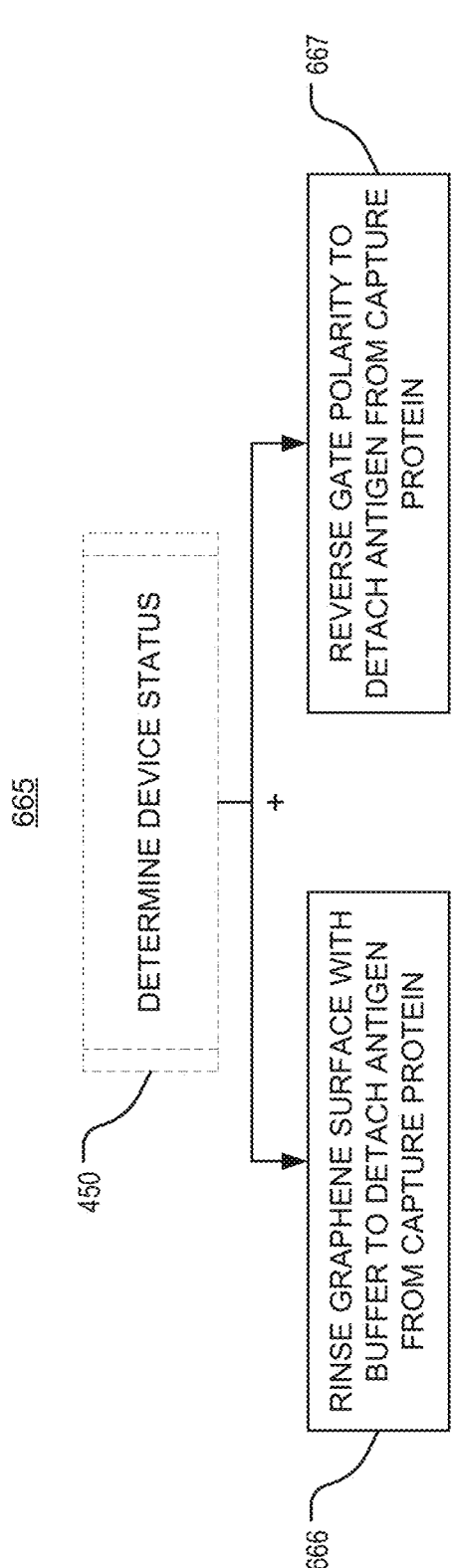
FIG. 6B is a flow diagram of a sub process of a method for monitoring viral loads in effluent, according to an exemplary embodiment of the present disclosure.

With reference now to FIG. 6B, sub process 665 of method 440 may proceed to perform one of two approaches upon a positive binary indication of the current status determination at sub process 450 of method 440.

At step 666 of sub process 665, the sensing surface of the graphene of each GFET of the GFET-based biosensor may be rinsed with a buffer solution to detach bound virus. The buffer may be provided to the fluidic channel by processing circuitry configured to control a pump that is fluidly connected to a buffer reservoir and to the fluidic channel of the VLMD. The buffer solution within the buffer reservoir may a volume sufficient to flood the fluidic channel. The buffer solution within the buffer reservoir may be PBS, in an example, or other buffer known to remove bound antigens from receptors. The buffer solution may be provided to the fluidic channel until it is determined at sub process 450 of method 440 that the binary indication of the current status of the VLMD is no longer positive.

Alternatively at step 667 of sub process 665, a gate polarity of each GFET of the GFET-based biosensor may be reversed. In other words, if a positive gate voltage of +100 mV is applied to a liquid gate of a GFET, a negative gate voltage of −100V may be applied in order to drive the virus from the capture protein (or drive the antigen from the receptor). Again, as above, the reversed gate polarity may be applied to the GFET of the GFET-based biosensor until the current status of the VLMD is determined to be negative at sub process 450 of method 440.

Of course, for either step 666 of sub process 665 or step 667 of sub process 665, respective processes may be performed until another threshold, beside that which is tied to sub process 450 of method 440, has been reached. For instance, each of step 666 and step 667 may continue until a conductance of each GFET of the GFET-based biosensor is below a minimum allowable threshold. The minimum allowable threshold may be a conductance value that reflects <5% bound virus, for instance.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them.

Embodiments of the subject matter described in this specification can be implemented as one or more computer programs, i.e., one or more modules of computer program instructions encoded on a tangible non-transitory program carrier for execution by, or to control the operation of data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be Supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

Figure 7:
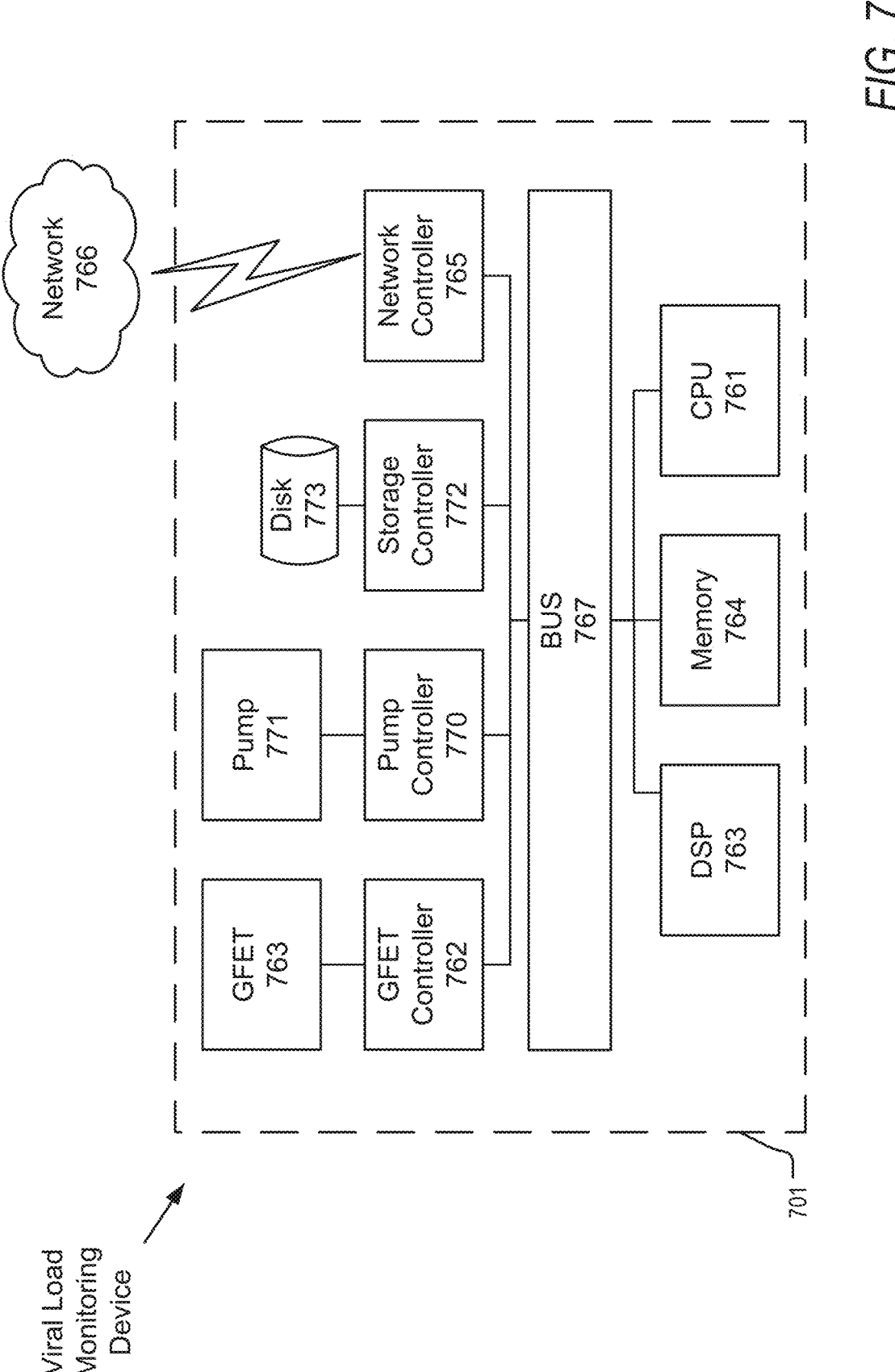
FIG. 7 is a hardware configuration of the device of FIG. 1, according to an exemplary embodiment of the present disclosure.

Returning to the Figures, FIG. 7 provides an exemplary hardware configuration of a VLMD of the preceding Figures, according to an embodiment of the present disclosure. Components of the hardware configuration of FIG. 7 may be included within a housing 701 of the VLMD or located remotely, as appropriate.

In FIG. 7, the VLMD includes a CPU 761 which performs the processes described above/below. The process data and instructions may be stored in memory 764. These processes and instructions may also be stored on a storage medium disk 773 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the VLMD communicates, such as a server or computer.

Further, the claimed advancements may be provided as a utility application, background daemon, or component of an operating system, or combination thereof, executing in conjunction with CPU 761 and an operating system such as Microsoft Windows 7, UNIX, Solaris, LINUX, Apple MAC-OS and other systems known to those skilled in the art.

The hardware elements in order to achieve the VLMD may be realized by various circuitry elements, known to those skilled in the art. The hardware elements may include CPU 761 which can include without limitation one or more processors, one or more special-purpose processors (such as digital signal processing (DSP) chips, graphics acceleration processors, application specific integrated circuits (ASICs), and/or the like), and/or other processing structure or means. For example, CPU 761 may be a Xenon or Core processor from Intel of America or an Opteron processor from AMD of America, or may be other processor types that would be recognized by one of ordinary skill in the art. Alternatively, the CPU 761 may be implemented on an FPGA, ASIC, PLD or using discrete logic circuits, as one of ordinary skill in the art would recognize. Further, CPU 761 may be implemented as multiple processors cooperatively working in parallel to perform the instructions of the inventive processes described above. The above-described processors can be specially-programmed to perform operations including, among others, image processing and data processing. Some embodiments may have a separate DSP 763, depending on desired functionality.

The VLMD in FIG. 7 also includes a network controller 765, such as an Intel Ethernet PRO network interface card from Intel Corporation of America, for interfacing with network 766 connected to a monitoring station, public health database, and the like. As can be appreciated, the network 766 can be a public network, such as the Internet, or a private network such as an LAN or WAN network, or any combination thereof and can also include PSTN or ISDN subnetworks. The network 766 can also be wired, such as an Ethernet network, or can be wireless such as a cellular network including EDGE, 3G and 4G wireless cellular systems. The wireless network can also be WiFi, Bluetooth, or any other wireless form of communication that is known.

The VLMD further includes a GFET controller 762, which may be integrated with the CPU 761, may be a microcontroller configured to control each GFET of the GFET-based biosensor. The microcontroller of the GFET may be, or may perform functions similar to, a semiconductor analyzer and probe station such as a 2634B semiconductor analyzer and probe station (Keithley Instruments, Cleveland, OH). Accordingly, the microcontroller may be configured to provide bias voltages, gate voltages, and to measure currents across source-drain electrodes for each of the GFETs of the VLMD.

A pump controller 770, which may be integrated with the CPU 761, is also provided in the VLMD. The pump controller 770 may be, for instance, an AT89C2051, and may be connected to and in control of pump 771, which is fluidly connected to the buffer reservoir, in order to provide buffer solution to the fluidic channel when required.

The general purpose storage controller 772 connects the storage medium disk 773 with communication bus 767, which may be an ISA, EISA, VESA, PCI, or similar, for interconnecting all of the components of the VLMD. A description of the general features and functionality of the pump 771 as well as the pump controller 770, the storage controller 772, the network controller 765, and the GFET controller 762 is omitted herein for brevity as these features are known.

During the COVID-19 pandemic, the development of highly sensitive and rapid biosensing devices has become increasingly important. The present disclosure describes a COVID-19 GFET-based biosensor in which the SARS-CoV-2 spike antibody is conjugated to a sensing surface of a graphene channel. The sensor may detect SARS-CoV-2 virus in effluent and, therefore, the sensor platform provides simple, rapid, and highly responsive detection of the SARS-CoV-2 virus in the field and in a continuous manner. Moreover, this technology could be adapted for diagnosis of other emerging viral diseases.

While this specification contains many specific implementation details, these should not be construed as limitations on the scope of what may be claimed, but rather as descriptions of features that may be specific to particular embodiments.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A system for viral monitoring in effluent, comprising a biosensor including at least one field-effect transistor along a length of an apparatus, the at least one field-effect transistor having one or more capture proteins conjugated thereto, the one or more capture proteins being configured to bind a virus in the effluent, and a fluidic channel arranged above the at least one field-effect transistor and along the length of the apparatus such that fluid of the effluent flows over the at least one field-effect transistor via the fluidic channel, and processing circuitry configured to apply a gate voltage to each of the at least one field-effect transistor, measure a conductance across each of the at least one field-effect transistor, a change in the conductance being based on an amount of the virus bound to the one or more capture proteins, compare the measured conductance across each of the at least one field-effect transistor to a threshold conductance, and transmit, to a computing device and when the comparison indicates the measured conductance across each of the at least one field-effect transistor satisfies the threshold conductance, information indicating a presence of the virus in the effluent.

(2) The system according to (1), wherein the at least one field-effect transistor is a graphene-based field-effect transistor.

(3) The system according to either (1) or (2), wherein the one or more capture proteins are SARS-CoV-2 spike antibodies.

(4) The system according to any one of (1) to (3), wherein the at least one field-effect transistor is liquid-gated by the effluent flowing over the at least one field-effect transistor.

(5) The system according to any one of (1) to (4), wherein the processing circuitry is configured to reverse a polarity of the applied gate voltage in order to reduce the amount of the virus bound to the one or more capture proteins when the comparison indicates the measured conductance across each of the at least one graphene-based field-effect transistor satisfies the threshold conductance, and maintain the reversed polarity of the applied gate voltage until the measured conductance across each of the at least one field-effect transistor does not satisfy the threshold conductance.

(6) The system according to any one of (1) to (5), further comprising a reservoir containing a buffer solution, wherein the processing circuitry is configured to provide, via a pump, the buffer solution to the fluidic channel when the comparison indicates the measured conductance across each of the at least one graphene-based field-effect transistor satisfies the threshold conductance, the provided buffer solution flowing over the at least one field-effect transistor in order to reduce the amount of the virus bound to the one or more capture proteins, the provided buffer solution being provided to the fluidic channel until the measured conductance across each of the at least one field-effect transistor does not satisfy the threshold conductance.

(7) The system according to any one of (1) to (6), wherein the processing circuitry is further configured to transmit the information indicating the presence of the virus in the effluent to the computing device by wireless communication.

(8) The system according to any one of (1) to (7), wherein the virus is bound to the one or more capture proteins via an inactivated component of the virus.

(9) An apparatus for monitoring of viral load in effluent, comprising processing circuitry configured to apply a gate voltage to each of at least one field-effect transistor disposed along a length of an apparatus, the at least one field-effect transistor having one or more capture proteins conjugated thereto, the one or more capture proteins being configured to bind a virus in the effluent, measure a conductance across each of the at least one field-effect transistor, a change in the conductance being based on an amount of the virus bound to the one or more capture proteins, compare the measured conductance across each of the at least one field-effect transistor to a threshold conductance, and transmit, to a computing device and when the comparison indicates the measured conductance across each of the at least one field-effect transistor satisfies the threshold conductance, information indicating a presence of the virus in the effluent, wherein the gate voltage is applied to a fluidic channel arranged above the at least one field-effect transistor and along the length of the apparatus such that fluid of the effluent flows over the at least one field-effect transistor via the fluidic channel.

(10) The apparatus according to (9), wherein the at least one field-effect transistor is a graphene-based field-effect transistor.

(11) The apparatus according to either (9) or (10), wherein the one or more capture proteins are SARS-CoV-2 spike antibodies.

(12) The apparatus according to any one of (9) to (11), wherein the processing circuitry is configured to reverse a polarity of the applied gate voltage in order to reduce the amount of the virus bound to the one or more capture proteins when the comparison indicates the measured conductance across each of the at least one graphene-based field-effect transistor satisfies the threshold conductance, and maintain the reversed polarity of the applied gate voltage until the measured conductance across each of the at least one field-effect transistor does not satisfy the threshold conductance.

(13) The apparatus according to any one of (9) to (12), wherein the processing circuitry is configured to provide, via a pump, a buffer solution to the fluidic channel when the comparison indicates the measured conductance across each of the at least one graphene-based field-effect transistor satisfies the threshold conductance, the provided buffer solution flowing over the at least one field-effect transistor in order to reduce the amount of the virus bound to the one or more capture proteins, the provided buffer solution being provided to the fluidic channel until the measured conductance across each of the at least one field-effect transistor does not satisfy the threshold conductance.

(14) The apparatus according to any one of (9) to (13), wherein the processing circuitry is further configured to transmit the information indicating the presence of the virus in the effluent to the computing device by wireless communication.

(15) The apparatus according to any one of (9) to (14), wherein the virus is bound to the one or more capture proteins via an inactivated component of the virus.

(16) A method for monitoring of viral load in effluent, comprising applying, by processing circuitry, a gate voltage to each of at least one graphene-based field-effect transistor disposed along a length of an apparatus, the at least one graphene-based field-effect transistor having one or more capture proteins conjugated thereto, the one or more capture proteins being configured to bind a virus in the effluent, measuring, by the processing circuitry, a conductance across each of the at least one graphene-based field-effect transistor, a change in the conductance being based on an amount of the virus bound to the one or more capture proteins, comparing, by the processing circuitry, the measured conductance across each of the at least one graphene-based field-effect transistor to a threshold conductance, and transmitting, by the processing circuitry to a computing device, information indicating a presence of the virus in the effluent to a computing device when the comparing indicates the measured conductance across each of the at least one graphene-based field-effect transistor satisfies the threshold conductance, wherein the one or more capture proteins are one or more SARS-CoV-2 spike antibodies.

(17) The method according to (16), wherein the gate voltage is applied to a fluidic channel arranged above the at least one graphene-based field-effect transistor, along the length of the apparatus, and fluid of the effluent flows over the at least one graphene-based field-effect transistor via the fluidic channel.

(18) The method according to either (16) or (17), further comprising reversing, by the processing circuitry and when the comparing indicates the measured conductance across each of the at least one graphene-based field-effect transistor satisfies the threshold conductance, a polarity of the applied gate voltage in order to reduce the amount of the virus bound to the one or more SARS-CoV-2 spike antibodies, and maintaining, by the processing circuitry, the reversed polarity of the applied gate voltage until the measured conductance across each of the at least one graphene-based field-effect transistor does not satisfy the threshold conductance.

(19) The method according to any one of (16) to (18), further comprising providing, by processing circuitry and via a pump, a buffer solution to the fluidic channel when the comparing indicates the measured conductance across each of the at least one graphene-based field-effect transistor satisfies the threshold conductance, the provided buffer solution flowing over the at least one graphene-based field-effect transistor in order to reduce the amount of the virus bound to the one or more SARS-CoV-2 spike antibodies, the provided buffer solution being provided to the fluidic channel until the measured conductance across each of the at least one graphene-based field-effect transistor does not satisfy the threshold conductance.

(20) The method according to any one of (16) to (19), further comprising transmitting, by the processing circuitry, the information indicating the presence of the virus in the effluent to the computing device via wireless communication.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system for viral monitoring in sewage wastewater in a sewage collection or treatment system, comprising:

a single sensor having a plurality of graphene field-effect transistors configured to bind SARS-COV-2; and circuitry configured to repeatedly monitor and determine presence of SARS-COV-2 in the sewage wastewater, wherein the circuitry is configured to apply a gate voltage to each of the plurality of graphene field-effect transistors, measure a conductance across each of the plurality of graphene field-effect transistors, a value of the conductance being based on an amount of the SARS-COV-2 bound to the plurality of graphene field-effect transistors, compare the measured conductance across each of the plurality of graphene field-effect transistors to respective threshold conductances, the threshold conductances being different for each of the plurality of graphene field-effect transistors, determine whether levels of the SARS-COV-2 in the sewage wastewater exceed a predetermined threshold based upon whether the measured conductance for each of the plurality of graphene field-effect transistors exceeds the threshold conductance, and determine whether a predetermined number of the plurality of graphene field-effect transistors have the measured conductance satisfying the threshold conductance.

2. The system according to claim 1, wherein each of the plurality of graphene field-effect transistors comprises one or more proteins configured to bind the SARS-COV-2 in the sewage wastewater.

3. The system according to claim 2, wherein the one or more proteins are SARS-COV-2 spike antibodies.

4. The system according to claim 1, further comprising a channel arranged above the plurality of graphene field-effect transistors to cause fluid of the sewage wastewater to flow over the plurality of graphene field-effect transistors via the channel.

5. An apparatus for viral monitoring in sewage wastewater in a sewage collection or treatment system, comprising:

a housing;

a single sensor having a plurality of graphene field-effect transistors configured to bind SARS-COV-2; and circuitry configured to repeatedly monitor and determine presence of SARS-COV-2 in the sewage wastewater, wherein the single sensor and the circuitry are mounted in the housing, and the circuitry is configured to apply a gate voltage to each of the plurality of graphene field-effect transistors, measure a conductance across each of the plurality of graphene field-effect transistors, a value of the conductance being based on an amount of the SARS-COV-2 bound to the plurality of graphene field-effect transistors, compare the measured conductance across each of the plurality of graphene field-effect transistors to respective threshold conductances, the threshold conductances being different for each of the plurality of graphene field-effect transistors, determine whether levels of the SARS-COV-2 in the sewage wastewater exceed a predetermined threshold based upon whether the measured conductance for each of the plurality of graphene field-effect transistors exceeds the threshold conductance, and determine whether a predetermined number of the plurality of graphene field-effect transistors have the measured conductance satisfying the threshold conductance.

6. The apparatus according to claim 5, wherein each of the plurality of graphene field-effect transistors comprises one or more proteins configured to bind the SARS-COV-2 in the sewage wastewater.

7. The apparatus according to claim 6, wherein the one or more proteins are SARS-COV-2 spike antibodies.

8. A method for viral monitoring in sewage wastewater in a sewage collection or treatment system, comprising:

repeatedly monitoring, by circuitry and a single sensor comprising a plurality of graphene field-effect transistors configured to bind a virus;

measuring, by the circuitry, a conductance across each of the plurality of graphene field-effect transistors, a value of the conductance being based on an amount of the virus bound to the plurality of graphene field-effect transistors;

comparing, by the circuitry, the measured conductance across each of the plurality of graphene field-effect transistors to respective threshold conductances the threshold conductances being different for each of the plurality of graphene field-effect transistors;

determining whether a predetermined number of the plurality of graphene field-effect transistors have the measured conductance satisfying the threshold conductance; and determining, by the circuitry, presence of SARS-COV-2 in the sewage wastewater, wherein each of the plurality of graphene field-effect transistors comprises one or more proteins configured to bind the SARS-COV-2 in the sewage wastewater.

9. The method according to claim 8, wherein the threshold conductance for one of the plurality of graphene field-effect transistors located at an upstream position in the sewage collection or treatment system is larger than the threshold conductance for another one of the plurality of graphene field-effect transistors located at a downstream position in the sewage collection or treatment system.

10. The method according to claim 8, wherein the determining comprises determining whether a majority of the plurality of graphene field-effect transistors satisfy the threshold conductance.

11. The system according to claim 1, wherein the threshold conductance for one of the plurality of graphene field-effect transistors located at an upstream position in the system is larger than the threshold conductance for another one of the plurality of graphene field-effect transistors located at a downstream position in the system.

12. The system according to claim 1, wherein the circuitry is further configured to determine whether a majority of the plurality of graphene field-effect transistors satisfy the threshold conductance.

13. The system according to claim 4, comprising a pump fluidly connected to a buffer fluid reservoir and to the channel, wherein the circuitry is further configured to control the pump to supply the buffer fluid to the channel to remove the SARS-COV-2 bound to the plurality of graphene field-effect transistors.

14. The system according to claim 13, wherein the circuitry is further configured to continue to supply the buffer fluid until the conductance of each the plurality of graphene field-effect transistors is below a second predetermined threshold.

* * * * *